(12) United States Patent
Nardeo et al.

(10) Patent No.: US 9,352,129 B2
(45) Date of Patent: May 31, 2016

(54) INTRODUCER ASSEMBLY WITH CAP AND METHOD OF USING SAME

(75) Inventors: Mahase Nardeo, Collegeville, PA (US); William J. McCreight, Warminster, PA (US)

(73) Assignee: Medical Components, Inc., Harleysville, PA (US)

( * ) Notice: Subject to any disclaimer, the term of this patent is extended or adjusted under 35 U.S.C. 154(b) by 1495 days.

(21) Appl. No.: 12/332,025

(22) Filed: Dec. 10, 2008

(65) Prior Publication Data

US 2009/0157006 A1    Jun. 18, 2009

Related U.S. Application Data

(60) Provisional application No. 61/007,613, filed on Dec. 13, 2007.

(51) Int. Cl.
*A61M 25/06* (2006.01)
*A61M 25/00* (2006.01)

(52) U.S. Cl.
CPC ....... *A61M 25/0662* (2013.01); *A61M 25/0097* (2013.01)

(58) Field of Classification Search
CPC ..................... A61M 25/0662; A61M 25/0097; A61M 39/06; A61M 2025/0681; A61M 2039/062
USPC ........................................ 604/167.03, 167.04
See application file for complete search history.

(56) References Cited

U.S. PATENT DOCUMENTS

| | | | |
|---|---|---|---|
| 4,610,665 A | | 9/1986 | Matsumoto et al. |
| 4,932,633 A | | 6/1990 | Johnson et al. |
| 5,085,645 A | | 2/1992 | Purdy et al. |
| 5,250,033 A | | 10/1993 | Evans et al. |
| 5,304,142 A | | 4/1994 | Liebl et al. |
| 5,423,762 A | | 6/1995 | Hillstead |
| 5,603,702 A | * | 2/1997 | Smith et al. .................... 604/256 |
| 5,613,954 A | * | 3/1997 | Nelson et al. ............. 604/167.03 |
| 5,800,451 A | * | 9/1998 | Buess et al. .................... 606/185 |
| 5,868,714 A | * | 2/1999 | Danks ........................... 604/256 |
| 5,911,710 A | | 6/1999 | Barry et al. |
| 6,083,207 A | | 7/2000 | Heck |
| 6,488,674 B2 | | 12/2002 | Becker et al. |
| 6,764,464 B2 | | 7/2004 | McGuckin, Jr. et al. |
| 6,827,710 B1 | | 12/2004 | Mooney et al. |
| 7,081,106 B1 | * | 7/2006 | Guo et al. ................ 604/167.06 |
| 7,422,571 B2 | | 9/2008 | Schweikert et al. |
| 7,798,991 B2 | * | 9/2010 | Insignares .................. 604/93.01 |
| 7,842,013 B2 | * | 11/2010 | Haberland et al. ........ 604/167.03 |
| 2004/0102738 A1 | | 5/2004 | Dikeman et al. |
| 2004/0143219 A1 | | 7/2004 | Lee et al. |
| 2005/0010238 A1 | | 1/2005 | Potter et al. |
| 2005/0261630 A1 | * | 11/2005 | Mottola et al. ............ 604/167.04 |
| 2006/0135978 A1 | * | 6/2006 | Franer .......................... 606/185 |
| 2006/0229564 A1 | * | 10/2006 | Andersen et al. ........ 604/167.03 |

(Continued)

*Primary Examiner* — Aarti B Berdichevsky
(74) *Attorney, Agent, or Firm* — Fox Rothschild LLP

(57) ABSTRACT

An introducer sheath assembly (10) having a sheath tube (12), a hub (16), a valve (30) and a valve-retaining cap (50) on the proximal end of the hub. The cap (50) is so secured to the hub (16) as to have a closed, locked position and also an open position permitting access to the interior of the hub and the valve (30) while the cap (50) remains secured to the hub (16).

16 Claims, 4 Drawing Sheets

(56) References Cited

U.S. PATENT DOCUMENTS

| | | | |
|---|---|---|---|
| 2007/0135778 A1* | 6/2007 | Murray et al. | 604/317 |
| 2008/0033371 A1* | 2/2008 | Updegraff et al. | 604/263 |
| 2008/0161758 A1* | 7/2008 | Insignares | 604/167.04 |
| 2008/0171987 A1* | 7/2008 | Franer et al. | 604/167.03 |
| 2009/0082731 A1* | 3/2009 | Moreno | 604/158 |
| 2009/0143732 A1* | 6/2009 | O'Connor et al. | 604/151 |
| 2010/0042070 A1* | 2/2010 | Gill et al. | 604/513 |
| 2011/0046566 A1* | 2/2011 | Elahi et al. | 604/214 |

* cited by examiner

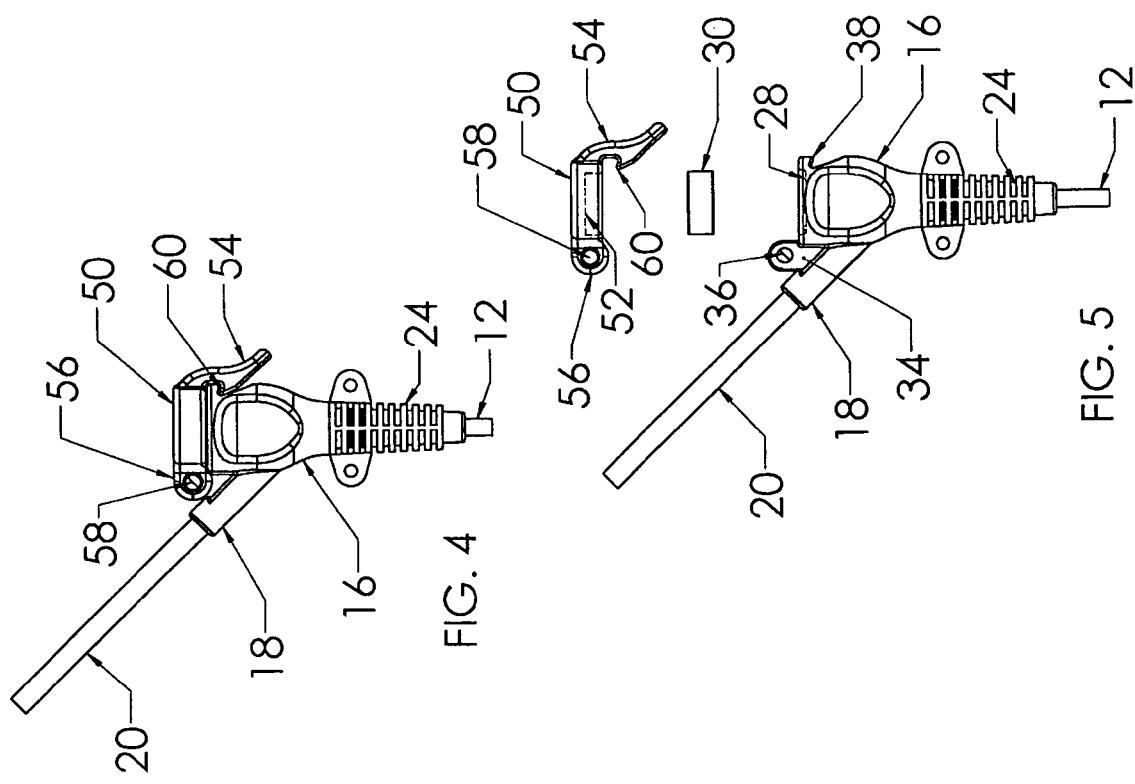

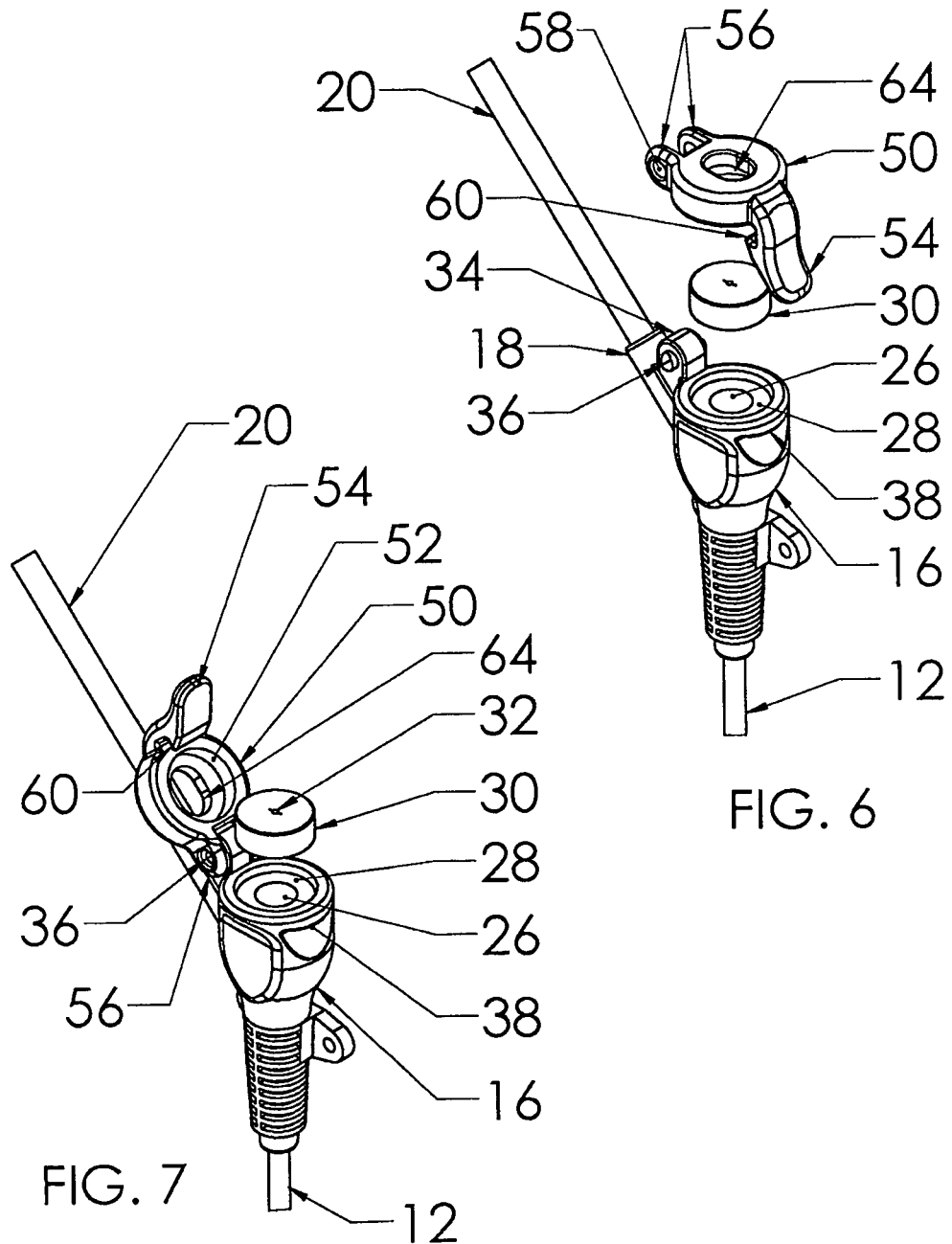

INTRODUCER ASSEMBLY WITH CAP AND METHOD OF USING SAME

CROSS-REFERENCE TO RELATED APPLICATIONS

This application claims priority from U.S. Provisional Patent Application Ser. No. 61/007,613, filed Dec. 13, 2007.

FIELD OF THE INVENTION

This relates to the field of medical devices, and more particularly to catheter introducer sheath assemblies.

BACKGROUND OF THE INVENTION

Catheters are often used for the delivery and withdrawal of fluids to and from a blood vessel in a patient, respectively. The fluids may be medication that is administered to the patient, or blood that is withdrawn from the patient. The catheter may also be used for hemodialysis, in which blood is withdrawn from the patient, purified and returned simultaneously through respective lumens of the catheter, and much of the catheter remains within the patient's vasculature for an extended period of time for repeated treatments.

Typically, to insert a catheter into a blood vessel, the blood vessel is located by known methods. An aspirating needle is inserted into the vessel to confirm placement within the vessel. A guide wire is then inserted through a proximal end of the aspirating needle and into the vessel. The aspirating needle is withdrawn by sliding the needle proximally over the guide wire, leaving the guide wire within the vessel. If a catheter with a sufficiently hard wall is being used, the catheter may be slid over the guide wire, directly into the vessel.

However, for some catheters, particularly soft walled catheters, a dilator is required to dilate the vessel at the insertion point in order to accommodate the insertion of the catheter. The dilator is typically inserted into a sheath and initially used as a dilator and sheath assembly. The assembly is inserted into the vessel over the guide wire, and the dilator is used to dilate the insertion opening in the vessel wall to permit catheter insertion thereinto. After the insertion opening is dilated, the dilator is removed proximally from the sheath. The sheath remains in the vessel to accommodate insertion of the catheter through the sheath and into the blood vessel, after which the sheath is removed from around the catheter, and the guidewire is withdrawn from the patient.

Conventional assemblies provide one-way valves within the introducer hub for hemostasis, that is, preventing blood flow from the patient's vasculature from the incision made for eventual catheter insertion; the valve seals the passageway while permitting insertion therethrough by a guidewire and a dilator and a catheter. Commonly, proximal caps are affixed to the proximal end of the introducer hub to retain the valve therewithin.

It commonly happens that blockages occur within introducer assemblies due to clotting of blood egressing the vascular incision formed for insertion of the catheter into the vasculature. Upon such an occasion, the introducer must be removed and replaced by another, a procedure that greatly extends the time needed and complicating the procedures followed by the practitioner to implant the catheter, thereby exposing the patient to greater risk of infection due to bleeding from the incision.

It is desired to provide an introducer assembly facilitating access by the practitioner to the passageway within the introducer hub to clear a blockage that may occur within the introducer.

BRIEF SUMMARY OF THE INVENTION

Briefly, the present invention provides an introducer assembly having a sheath, a hub, a valve disposed transverse to the passageway extending between the proximal and distal ends of the sheath and hub, and a cap for retaining the valve in proper position within the hub. The cap is attached to the hub at one side thereof by a pivot arrangement whereby the cap can be rotated by the practitioner between a closed position and an open position all while remaining secured to the assembly. A latch on the opposite side of the cap from the pivot arrangement latchingly secures to a catch on the opposite side of the hub to secure the cap in its closed position. When the cap is in the open position, the valve is removable by the practitioner permitting access to the introducer's passageway for clearance of a blockage whereafter the valve, or a replacement valve, if necessary, can be reinserted into position in the hub and the cap can be returned to its closed position, eliminating the necessity of removing the entire introducer assembly from the patient and replacing it with another.

The method of the present invention includes the steps of placing an introducer assembly in position accessing the vasculature of the patient and having a passageway extending therethrough between a distal end and a proximal end, the assembly including a valve-retention cap movably affixed to the assembly's proximal end between a closed position retaining the valve therein and an open position permitting access to the introducer passageway, moving the proximal cap to the open position, removing the blockage, and moving the cap to its closed position.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIGS. 4 and 5 are elevation and exploded elevation views, respectively, of the hub assembly of the introducer sheath of FIGS. 1 to 3, showing the introducer hub, the extension tube and the cap of the present invention; and FIGS. 6 and 7 are, respectively, an exploded isometric view of the proximal end, and an isometric view of the proximal introducer sheath end with the cap attached to the introducer hub and rotated to an open position with the valve exploded outwardly from the hub, exposing the passageway.

DETAILED DESCRIPTION OF THE INVENTION

Figure 1:
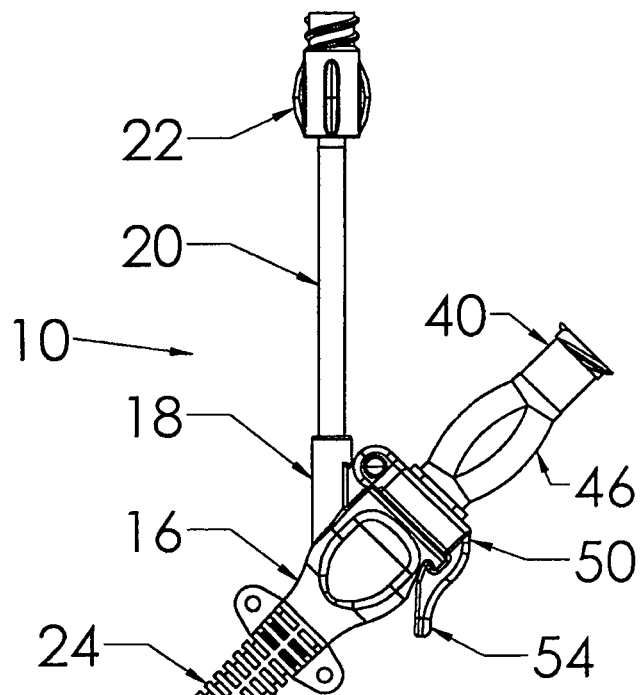
FIG. 1 is an isometric view of an introducer sheath with dilator inserted therethrough and also showing an extension tube extending from a side port of the introducer hub.

In the drawings, like numerals indicate like elements throughout. Certain terminology is used herein for convenience only and is not to be taken as a limitation on the present invention. The terms "distal" and "proximal" refer, respectively, to directions closer to and away from the insertion tip of a catheter in an implantable catheter assembly. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Figure 2:
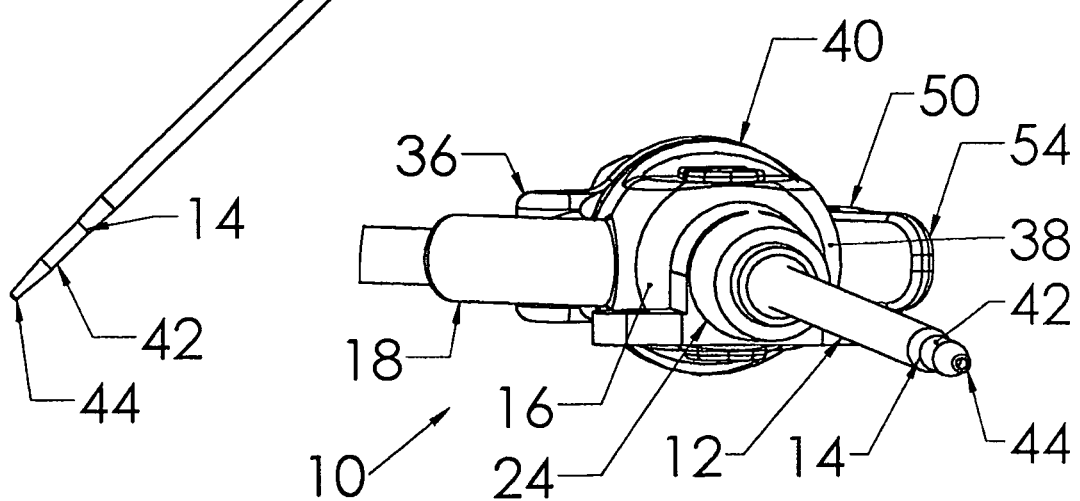
FIG. 2 is an isometric distal end view of the assembly of FIG. 1.

Introducer assembly 10 is seen in FIGS. 1 and 2, and includes an elongate tubular sheath 12 extending to a distal end 14, a hub 16 affixed to a proximal end of the sheath 12 and having a side port 18 from which extends an extension tube 20 with luer fitting 22, and a strain relief 24 at a distal end of the hub 16 and around the tubular sheath 12. A dilator 40 includes an elongate dilator shaft 42 extending from a distal tip 44 to a proximal end onto which is affixed a dilator hub 46; the dilator's distal tip 44 protrudes beyond the distal end 14 of the tubular introducer sheath 12 when the dilator is fully inserted into and through the introducer assembly 10.

Figure 3:
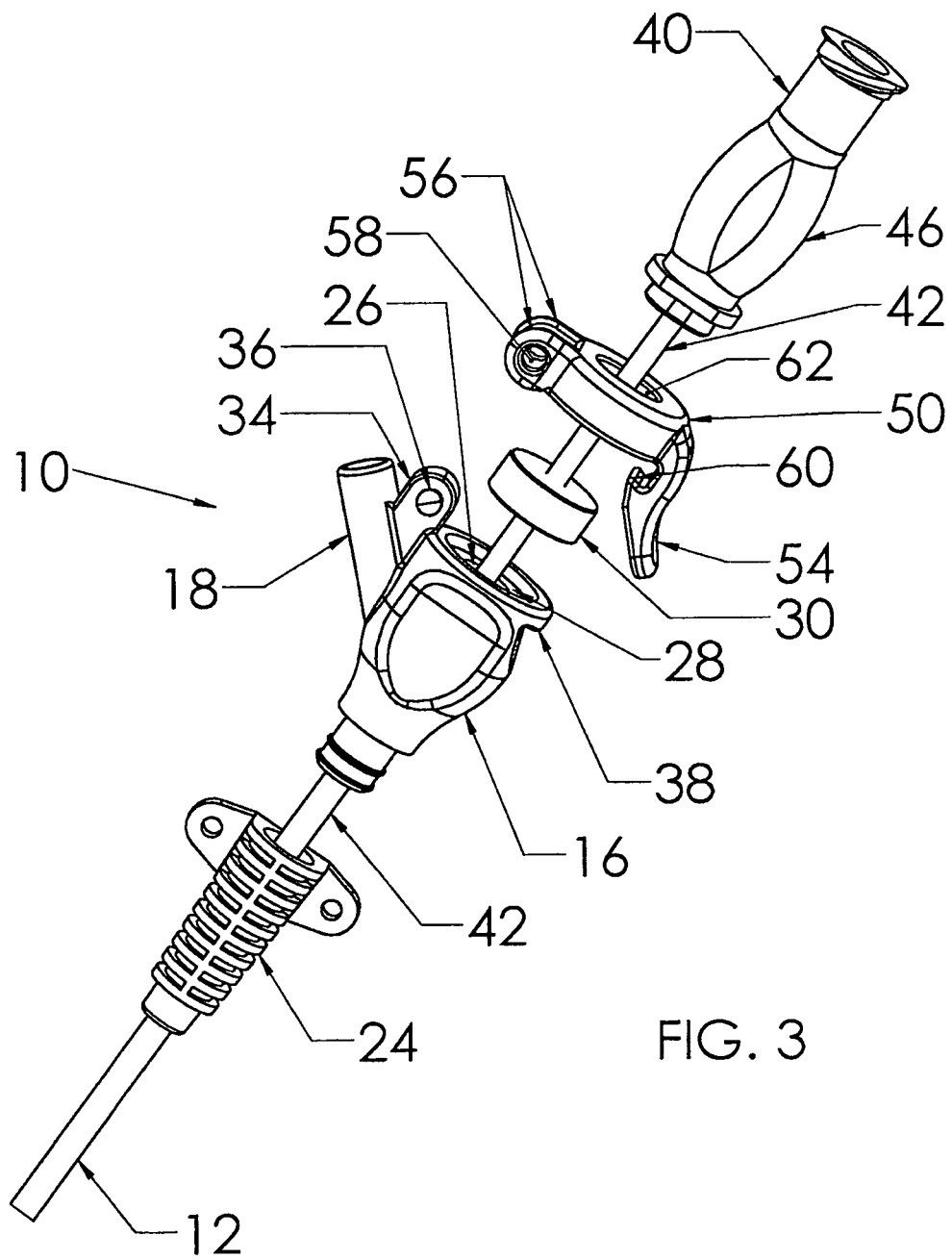
FIG. 3 is an enlarged isometric view of the proximal end of the assembly of FIG. 1 with the components shown exploded from the introducer sheath's elongate tube.

With reference to FIG. 3, hub 16 defines therethrough a passageway 26 extending to the passageway of the sheath 12. Recessed into the proximal end of the hub 16 is a valve seat portion 28 into which is placed a valve 30 that preferably includes a slit 32 (see FIG. 7) at the valve center enabling insertion therethrough of dilator shaft 42 and eventually a catheter (not shown). Also, the proximal end of the hub includes on one side a cap capture tab 34 projecting proximally that includes pivot pins 36 projecting laterally from both sides thereof. On the opposite side of the hub proximal end from tab 34 is a catch 38 to which the cap 50 will latch in its closed position.

Cap 50 includes a recess 52 (see FIGS. 5 and 7) along its distal surface defining a valve seat portion, and when cap 50 is attached to the hub 16 and in its closed position, retains valve 30 compressed in position within the valve seat 28, 52. Referring to FIGS. 3 to 7, cap 50 is seen to have a lift tab 54 depending from one side thereof that will extend alongside the hub when cap 50 is in position but project somewhat outwardly enabling manual grasping thereof to rotate cap 50 to an open position, as shown in FIG. 7. Cap 50 will pivot as a result of cooperating tabs 56 on the opposite cap side from lift tab 54, which tabs includes holes 58 therethrough associated with pivot pins 36 of cap capture tab 34 of hub 16. A latch ledge 60 is defined on the inner surface of lift tab 54 that latches to catch 38 of hub 16, to secure cap 50 in its closed position. Proximal aperture 62 of cap 50 permits insertion thereinto of dilator shaft 42 and eventually the catheter (not shown); additionally, proximal aperture 62 may include threads or other features that cooperate with a complementary locking section of the dilator hub 46 to releasably lock the dilator to the introducer sheath assembly.

With the present invention, the cap remains secured to the hub not only in the closed position but also in its open position and is thus not a loose piece, if the practitioner must obtain access to the introducer sheath passageway to remove a blockage such as a clot.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. An introducer assembly for use in insertion of a medical device, such as a vasculature catheter, into a patient, the introducer assembly comprising:
    an introducer sheath tube, a hub having a proximal hub opening and a distal hub opening and a passageway extending between the openings, the hub is secured to a proximal end of the sheath tube such that the hub passageway is aligned with a passageway of the sheath tube, a valve disposed at least partially within the hub for sealing the hub passageway while permitting insertion therethrough of a medical device, the valve sized and configured such that the valve is passable through the proximal hub opening; and a valve-retaining cap,
    wherein the cap is so affixed to the hub at a proximal end thereof that the cap is movable between a closed position wherein the cap closes at least a portion of the proximal hub opening such that the valve is prevented from passing through the hub proximal opening, and an open position wherein the cap is clear of the proximal hub opening such that the valve is passable through the proximal hub opening thus permitting access to the hub and sheath passageways through the proximal hub opening while the cap remains secured to the hub and the hub remains secured to the sheath tube.

2. The introducer assembly of claim 1, wherein the hub proximal end and a distal end of the cap each define recesses together comprising a valve seat, the hub and cap compressing the valve between them, and into a retained position within the assembly when the cap is in the closed position.

3. The introducer assembly of claim 1, wherein the cap includes a through passageway co-axial with the hub passageway when the cap is in the closed position, the through passageway having a diameter smaller than a diameter of the proximal hub opening.

4. The introducer assembly of claim 1, wherein the hub includes a catch and the cap includes a latch cooperable with the catch to lock the cap in the closed position.

5. The introducer assembly of claim 4, wherein the cap includes a lift tab having an inside surface facing the hub when the cap is in the closed position and the latch is defined along the inside surface of the lift tab, the lift tab facilitating manual grasping thereof to unlatch the cap to move the cap to the open position.

6. The introducer assembly of claim 1, wherein the hub includes a cap capture section and the cap includes a cooperating capture section that secures the cap to the hub while permitting the cap to be moved between the closed position and the open position with respect to the hub.

7. The introducer assembly of claim 6, wherein the cap capture section is at least one tab projecting from the hub and each at least one tab defines one of pivot holes extending into sides thereof or pivot pins extending laterally from sides thereof, and the cooperating capture section is at least one tab projecting from the cap and each defines the other of pivot holes extending into sides thereof or pivot pins extending laterally from sides thereof such that the cooperating capture section is snap fitted to the cap capture section such that the pivot pins extend into the pivot holes and thereafter permit pivoting of the cap with respect to the hub between the open and closed positions.

8. The introducer assembly of claim 7, wherein the cap capture section is one tab having pivot pins projecting laterally from both sides thereof, and the cooperating capture section of the cap is defined by two tabs that are positionable to respective sides of the one tab and include pivot holes into which are received the pivot pins of the one tab.

9. The introducer assembly of claim 1, wherein the proximal end of the hub includes a cap capture section and the cap includes a cooperating capture section that secures the cap to the hub while permitting the cap to be moved between the closed position and the open position with respect to the hub, and wherein the hub includes a catch on an opposite side from the cap capture section and the cap includes a latch cooperable with the catch to lock the cap in the closed position and to unlock the cap and permit movement to the open position.

10. The introducer assembly of claim 9, wherein the cap includes a lift tab having an inside surface facing the hub when the cap is in the closed position and the latch is defined along the inside surface of the lift tab, the lift tab facilitating manual grasping thereof to unlatch the cap to move it to the open position.

11. The introducer assembly of claim 9, wherein the hub proximal end and a distal end of the cap each define recesses respectively thereinto together comprising a valve seat, the hub and cap compressing the valve between them, and into a retained position within the assembly when the cap is in the closed position.

12. The introducer assembly of claim 9, wherein the cap capture section is at least one tab projecting from the hub and each at least one tab defines one of pivot holes extending into sides thereof or pivot pins extending laterally from sides thereof, and the cooperating capture section is at least one tab projecting from the cap and each defines the other of pivot holes extending into sides thereof or pivot pins extending laterally from sides thereof such that the cooperating capture section is snap fitted to the cap capture section such that the pivot pins extend into the pivot holes and thereafter permit pivoting of the cap with respect to the hub between the open and closed positions.

13. The introducer assembly of claim 12, wherein the cap capture section is one tab having pivot pins projecting laterally from both sides thereof, and the cooperating capture section of the cap comprises two tabs that are positionable to respective sides of the one tab and define pivot holes into which are received the pivot pins of the one tab.

14. A method of using an introducer assembly, comprising the steps of:
placing an introducer assembly in position accessing vasculature of a patient with a valve-retaining cap of the introducer assembly in a closed position, the introducer assembly including a sheath with a passageway extending therethrough between a distal end and a proximal end, a hub secured to the sheath proximal end, the hub defining a proximal hub opening and a distal hub opening and a hub passageway extending between the openings and aligned with the sheath passageway, a valve positioned in and sealing the hub passageway, the valve sized and configured such that the valve is passable through the proximal hub opening, wherein the valve-retention cap is affixed to the hub and in the closed position, the valve-retention cap closes at least a portion of the proximal hub opening such that the valve is prevented from passing through the proximal hub opening;
moving the valve-retention cap to an open position wherein the valve-retention cap is affixed to the hub but clear of the proximal hub opening and removing the valve from the proximal hub opening for access to the hub and sheath passageways to permit removal of a blockage therefrom;
removing the blockage; and
replacing the valve and moving the cap to the closed position.

15. The method of claim 14, wherein the step of moving the valve-retention cap to the open position comprises pivoting the cap about a pivot joint with the hub.

16. The method of claim 14, wherein the introducer assembly further includes a dilator extending through an open passageway through the valve-retention cap, through the valve, through the hub and sheath passageways and out the sheath distal end, and the method further includes removing the dilator prior to the step of moving the valve-retention cap to the open position.

* * * * *